US010875235B2

(12) United States Patent
Yee et al.

(10) Patent No.: US 10,875,235 B2
(45) Date of Patent: Dec. 29, 2020

(54) BACTERICIDAL SURFACE PATTERNS

(71) Applicant: The Regents of the University of California, Oakland, CA (US)

(72) Inventors: Albert Fan Yee, Irvine, CA (US); Elena Liang, Irvine, CA (US); Nicole Ing, Irvine, CA (US); Markelle Gibbs, Irvine, CA (US); Mary Nora Dickson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/673,588

(22) Filed: Mar. 30, 2015

(65) Prior Publication Data

US 2015/0273755 A1 Oct. 1, 2015

Related U.S. Application Data

(60) Provisional application No. 61/973,697, filed on Apr. 1, 2014.

(51) Int. Cl.
| | |
|---|---|
| *B32B 3/10* | (2006.01) |
| *B29C 59/02* | (2006.01) |
| *B81C 1/00* | (2006.01) |
| *B29K 71/00* | (2006.01) |
| *B29K 69/00* | (2006.01) |

(Continued)

(52) U.S. Cl.
CPC ........ *B29C 59/026* (2013.01); *B81C 1/00206* (2013.01); *B29C 2059/023* (2013.01); *B29K 2025/06* (2013.01); *B29K 2069/00* (2013.01); *B29K 2071/00* (2013.01); *B29K 2081/06* (2013.01); *B29L 2007/001* (2013.01); *B81B 2203/0361* (2013.01); *B82Y 5/00* (2013.01); *B82Y 40/00* (2013.01); *Y10S 977/887* (2013.01); *Y10T 428/24893* (2015.01)

(58) Field of Classification Search
None
See application file for complete search history.

(56) References Cited

U.S. PATENT DOCUMENTS

| 6,106,552 A | 8/2000 | Lacombe et al. |
|---|---|---|
| 2003/0175325 A1 | 9/2003 | Chatelier et al. |

(Continued)

FOREIGN PATENT DOCUMENTS

| WO | WO 2013172794 A1 * 11/2013 | ........... B63B 59/045 |
|---|---|---|
| WO | 2015055656 A1  4/2015 | |

(Continued)

OTHER PUBLICATIONS

Optical Biomimetics: Materials and Applications edited by Maryanne Large Publication date Oct. 18, 2012.*

(Continued)

*Primary Examiner* — Christopher M Polley
(74) *Attorney, Agent, or Firm* — KPPB LLP

(57) ABSTRACT

The invention relates to imparting surfaces with nanometer sized structures that provide bactericidal properties to the surface and devices. In one embodiment, the present invention provides a bactericidal surface with nanometer sized pillars created by imprinting a softened polymer surface with a mold. In another embodiment, the nanometer sized pillars are part of a medical device with antibacterial properties.

35 Claims, 9 Drawing Sheets

(51) Int. Cl.
  *B29K 25/00* (2006.01)
  *B29K 81/00* (2006.01)
  *B82Y 5/00* (2011.01)
  *B82Y 40/00* (2011.01)
  *B29L 7/00* (2006.01)

(56) References Cited

U.S. PATENT DOCUMENTS

| | | |
|---|---|---|
| 2007/0168025 A1 | 7/2007 | Darougar et al. |
| 2007/0227428 A1* | 10/2007 | Brennan ............ B08B 17/06 114/67 R |
| 2008/0317982 A1 | 12/2008 | Hecht et al. |
| 2009/0194913 A1 | 8/2009 | Chang et al. |
| 2009/0266418 A1 | 10/2009 | Hu et al. |
| 2010/0036488 A1 | 2/2010 | de Juan, Jr. et al. |
| 2010/0239637 A1 | 9/2010 | Ciolino et al. |
| 2011/0125260 A1 | 5/2011 | Shen |
| 2011/0135814 A1 | 6/2011 | Miyauchi et al. |
| 2011/0160851 A1 | 6/2011 | Mueller-lierheim |
| 2013/0059113 A1* | 3/2013 | Hatton ............... B08B 17/06 428/116 |
| 2013/0244889 A1 | 9/2013 | Yim et al. |
| 2014/0305904 A1 | 10/2014 | Lan |
| 2015/0104622 A1* | 4/2015 | Chong ............... B63B 59/045 428/195.1 |
| 2019/0075789 A1 | 3/2019 | Yee et al. |
| 2019/0076573 A1 | 3/2019 | Yee et al. |
| 2019/0101669 A1 | 4/2019 | Yee et al. |

FOREIGN PATENT DOCUMENTS

| | | |
|---|---|---|
| WO | 2017156460 A1 | 9/2017 |
| WO | 2017160658 A1 | 9/2017 |
| WO | 2017156460 A8 | 5/2018 |

OTHER PUBLICATIONS

Natural Bactericidial Surfaces: Mechanical Rupture of Pseudomonas aeruginosa Cells by Cicada Wings Ivanova et al retieved on Aug. 6, 2017 https://www.researchgate.net/publication/225279133_Natural_Bactericidal_Surfaces_Mechanical_Rupture_of_Pseudomonas_aeruginosa_Cells_by_Cicada_Wings.*
https://www.researchgate.net/publication/6607642_Cicada_Wings_A_Stamp_from_Nature_for_Nanoimprint_Lithography Zhang et al Dec. 2006 (Year: 2006).*

Banerjee et al., Antifouling Coatings: Recent Developments in the Design of Surfaces That Prevent Fouling by Proteins, Bacteria, and Marine Organisms. Advanced Materials (Feb. 11, 2011), pp. 690-715, 23(6).
Chung et al., Impact of Engineered Surface Microtopography on Biofilm Formation of *Staphylococcus aureus*, Biointerphases (Jun. 2007), pp. 89-94, 2(2).
Hasan et al., Selective Bactericidal Activity of Nano-Patterned Superhydrophobic Cicada *Psaltoda claripennis* Wing Surfaces, Applied Microbiology and Biotechnology (Oct. 2013), pp. 9257-9261, 97(20).
Ivanova et al., Natural Bactericidal Surfaces: Mechanical Rupture of Pseudomonas aeruginosa Cells by Cicada Wings, Small (Aug. 20, 2012), pp. 2489-2494, 8(16).
Kirschner et al., Bio-Inspired Antifouling Strategies, Annual Review of Materials Research (2012), pp. 211-29, 42.
Liu et al., Bio-Inspired Design of Multiscale Structures for Function Integration, Nano Today (Apr. 2011), pp. 155-175, 6(2).
Pogodin et al., Biophysical Model of Bacterial Cell Interactions with Nanopatterned Cicada Wing Surfaces, Biophysical Journal (2013), pp. 835-840, 104(4).
Sun et al., Wetting Properties on Nanostructured Surfaces of Cicada Wings, Journal of Experimental Biology (Oct. 1, 2009), pp. 3148-3155, 212(19).
Yao et al., Atomic Force Microscopy and Theoretical Considerations of Surface Properties and Turgor Pressures of Bacteria. Colloids and Surfaces B: Biointerfaces (2002), pp. 213-230, 23.
Zhang et al., Cicada Wings: A Stamp from Nature for Nanoimprint Lithography, Small (Dec. 2006), pp. 1440-1443, 2(12).
International Preliminary Report on Patentability for International Application PCT/US2017/021908, Report dated Sep. 11, 2018, dated Sep. 20, 2018, 9 Pgs.
International Preliminary Report on Patentability for International Application PCT/US2017/021926, Report dated Sep. 18, 2018, dated Sep. 27, 2018, 7 Pgs.
International Search Report and Written Opinion for International Application No. PCT/US2017/021908, Search completed Jun. 23, 2017, dated Jul. 7, 2017, 12 Pgs.
International Search Report and Written Opinion for International Application No. PCT/US2017/021926, Search completed Apr. 25, 2017, dated Jun. 1, 2017, 8 Pgs.
Kopplmayr et al., "Nanoimprint Lithography on curved surfaces prepared by fused deposition modelling", Surface Topography: Metrology and Properties Jun. 2015, vol. 3, No. 2, 024003, 12 pgs.
Zhang et al., "Surface Modification of Polymethyl Methacrylate Intraocular Lenses by Plasma for Improvement of Antithrombogenicity and Transmittance", Applied Surface Science, vol. 255, pp. 6840-6845, Year (2009).

* cited by examiner (A)

(B)

BACTERICIDAL SURFACE PATTERNS

CROSS-REFERENCE TO RELATED APPLICATIONS

The present application claims the benefit of priority under 35 U.S.C. § 119(e) of provisional application Ser. No. 61/973,697, filed Apr. 1, 2014, the contents of which are hereby incorporated by reference.

FIELD OF INVENTION

The invention relates to the field of biotechnology, nanotechnology and medical devices. Specifically, the invention relates to surfaces with textures that are bactericidal.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cellular interactions with material surfaces are critical to the performance of medical devices and systems immersed in aqueous environments or are covered by an aqueous film. Much research has concerned host cell-substrate interaction of implanted medical devices; however, the interaction of bacterial cells, which in humans outnumber host cells at least 10 to 1, with the material surface is also important. The useful lifetime of biomedical implants can be greatly diminished by development of biofilms. A biofilm is composed of bacteria, proteins, and cells that adhere and aggregate on the material surface. Biofilm development begins when a single planktonic cell attaches to an available material surface in response to environmental cues, including nutrient availability and physicochemical forces. Once adhered to the material surface, the bacteria begin to proliferate, secreting extracellular polysaccharide substance (EPS) and forming multilayer cell clusters on the material surface to create the biofilm. Biofilm formation on an implanted medical device can cause persistent infection, especially if parts of the biofilms shed off into the bloodstream, eliciting immune response and triggering the release of harmful toxins in the body. Biofilms have been reported to account for over 80% of microbial infections in humans; in fact, many of undiagnosed chronic diseases are thought be of biofilm origin.

To date, most antibiofouling materials aim to prevent biofilm formation by utilizing antimicrobial agents to prevent cell proliferation, or employ chemical surface modifications, such as crosslinking with poly(ethylene glycol), that are thought to inhibit cell adhesion by preventing protein adsorption. Recently, selenium nanoparticles were proposed as a potential antibacterial coating for polymeric devices. However, neither are long-term solutions. In the case of antimicrobial agents, it is known that bacteria eventually develop resistance to them. Additionally, bacterial cells in biofilm are 10- to 1000-fold less susceptible to antimicrobial agents than the same bacteria in planktonic culture. In the case of surface chemical modifications, even unattached bacteria can secrete proteins that are adsorbed to a static surface. The addition of the protein layer will eventually mask the effects of such chemical modifications. In case of the selenium particles, high levels of selenium in the body can be toxic. In both cases, chemically modifying materials which are to be used in biomedical devices may have unknown effects upon biocompatibility and thereby increase the potential for harm and increase the burden for testing. Thus, there is a great need in the art for more effective methods and materials that prevent biofilm formation.

SUMMARY OF THE INVENTION

Various embodiments herein include an antibacterial composition comprising a surface comprising a surface coated with a plurality of nanopillars. In another embodiment, the surface is a hard plastic surface. In another embodiment, the plurality of nanopillars are spaced less than the width of a bacteria. In another embodiment, the plurality of nanopillars are spaced 10 to 500 nm apart. In another embodiment, the surface is a high temperature plastic. In another embodiment, the plurality of nanopillars are spaced apart by 300 nm or less. In another embodiment, the plurality of nanopillars are spaced apart by 700 nm or less. In another embodiment, the nanopillars are 25 to 500 nm in diameter. In another embodiment, the nanopillars are 700 nm or less in diameter. In another embodiment, the nanopillars are 100 nm or less in diameter. In another embodiment, the nanopillars are 30 nm or less in diameter. In another embodiment, the plurality of nanopillars are an array of pillars with circular cross sections. In another embodiment, the surface is a polymethylmethacrylate (PMMA) film. In another embodiment, the surface is a polymer film. In another embodiment, the surface is polycarbonate (PC), polystyrene (PS), polyetherether ketone (PEEK), or polysulfone (PSu). In another embodiment, the surface is made of a material resistant to repeated sterilization procedures. In another embodiment, the nanopillars are described in Table 3 herein.

Other embodiments include a method of preparing a bactericidal surface, comprising providing a surface, and modifying the surface by creating a plurality of nanostructures upon the surface. In another embodiment, the plurality of nanostructures are imprinted polymer nanostructures. In another embodiment, the plurality of nanostructures are created on polymethylmethacrylate (PMMA) film. In another embodiment, the plurality of nanostructures are created using nanoimprint lithography. In another embodiment, the plurality of nanostructures are imprinted a first time, followed by rotating by around 90 degrees, followed by imprinting a second time. In another embodiment, the nanostructures are pillars. In another embodiment, the nanostructures are made by imprinting polymer film. In another embodiment, the nanostructures are imprinted by lines spaced 200 to 300 nm apart. In another embodiment, the nanostructures are imprinted by lines 20 to 50 nm wide. In another embodiment, the nanostructures are imprinted by lines 50 to 100 nm wide. In another embodiment, the plurality of nanostructures are created by imprinting by a negative mold from hardened polydimethylsiloxane (PDMS). In another embodiment, the plurality of nanostructures are created by imprinting by a nickel mold. In another embodiment, the plurality of nanostructures are created by imprinting by a silicon mold.

Other embodiments include a bactericidal surface with one or more nanopillars. In another embodiment, the bactericidal surface does not result from chemical modifications made to the surface. In another embodiment, the bactericidal surface does not include a bactericide and/or silver nanoparticle. In another embodiment, the medical device is a biomedical implant. In another embodiment, the bactericidal surface is a polymer surface with adhesion control by surface nanotexture. In another embodiment, the bactericidal surface is a high temperature plastic.

Other embodiments include a bactericidal surface, comprising a surface modified by one or more nanostructures. In another embodiment, the nanostructures are imprinted polymer nanopillars. In another embodiment, the nanostructures are created on polymethylmethacrylate (PMMA) film using nanoimprint lithography. In another embodiment, the nanostructures are imprinted a first time, followed by rotating by around 90 degrees, followed by imprinting a second time. In another embodiment, the nanostructures are pillars made by imprinting PMMA film with lines spaced 200 to 300 nm apart. In another embodiment, the nanostructures are pillars made by imprinting lines 20 to 50 nm wide. In another embodiment, the nanostructures are pillars made by imprinting lines 50 to 100 nm wide.

Various embodiments include a method of preventing biofilm formation, comprising providing a polymer film, and creating a plurality of nanostructures upon the polymer film using nanoimprint lithography. In another embodiment, the plurality of nanostructures are nano-pillars. In another embodiment, the nanostructures are imprinted polymer nanostructures.

Other embodiments include a method of preparing an implantable device with antibacterial properties, comprising providing a device, and modifying the device to prevent bacteria adhesion by utilizing surface nanotexture without chemical modifications to the surface. In another embodiment, the device has a polymer surface. In another embodiment, the surface nanotexture comprises nanopillars. In another embodiment, the device is made of a material resistant to repeated sterilization procedures.

Other features and advantages of the invention will become apparent from the following detailed description, taken in conjunction with the accompanying drawings, which illustrate, by way of example, various embodiments of the invention.

BRIEF DESCRIPTION OF FIGURES

Exemplary embodiments are illustrated in the referenced figures. It is intended that the embodiments and figures disclosed herein are to be considered illustrative rather than restrictive.

DETAILED DESCRIPTION OF THE INVENTION

Figure 1:
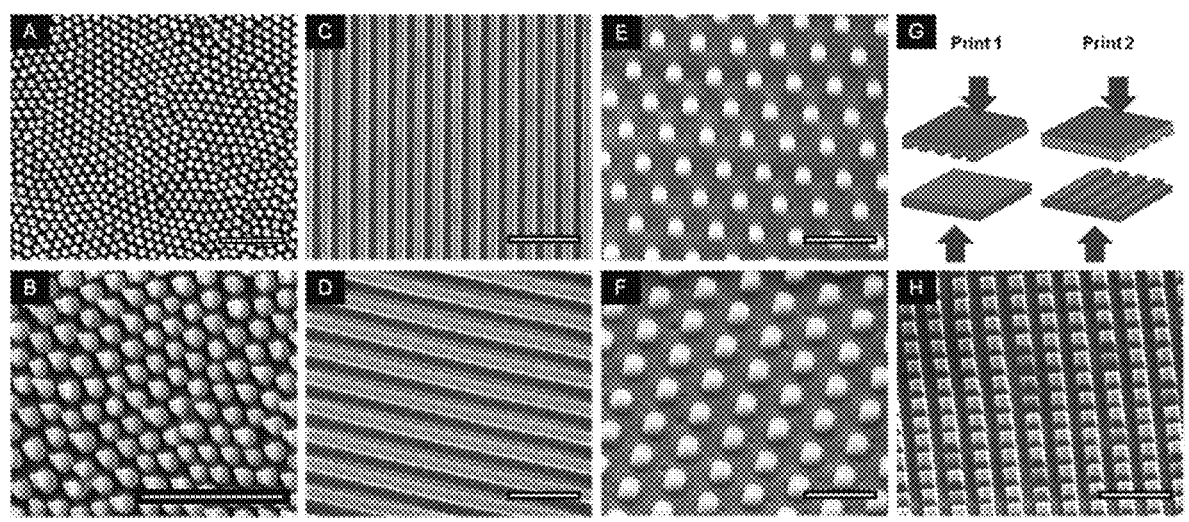
FIG. 1 depicts, in accordance with various embodiments of the present invention, nanostructures fabricated with nanoimprint lithography on PMMA film surface. The inventors were inspired by the surface of the cicada wing, shown in (A) and (B); (B) was taken at a higher magnification. Imprinted patterns include line gratings (C, D) round top pillars (E, F), and square top pillars (G). Width and spacing of line gratings in (D), designated at L2, is about twice that of the line gratings in (C), designated as L1. Likewise, the spacing between the pillars in (E), designated as P1, is about 100 nm less than the pillar spacing in (F), designated as P2. To fabricate the square pillars, we double-imprinted a line grating pattern using the line molds (gray) on the PMMA film (blue), as demonstrated in the schematic in (G). This double imprinting resulted in the grid pattern of square top pillars, designated at PS (H). Image of P1 were taken at a 30 degree tilt, while P2 and PS were taken at 45 degree tilt. P1, P2 and PS pillars are comparable to the nanostructures on the cicada wing surface.

All references cited herein, including the references cited therein, are incorporated by reference in their entirety as though fully set forth. Unless defined otherwise, technical and scientific terms used herein have the same meaning as commonly understood by one of ordinary skill in the art to which this invention belongs. The practice of the present invention will employ, unless indicated specifically to the contrary, conventional methods of molecular biology and recombinant DNA techniques within the skill of the art, many of which are described below for the purpose of illustration. Such techniques are fully explained in the literature. See, e.g., Singleton et al., Dictionary of Microbiology and Molecular Biology 4th ed., J. Wiley & Sons (New York, N.Y. 2012); March, Advanced Organic Chemistry Reactions, Mechanisms and Structure 5th ed., J. Wiley & Sons (New York, N.Y. 2001); and Sambrook and Russel, Molecular Cloning: A Laboratory Manual 4th ed., Cold Spring Harbor Laboratory Press (Cold Spring Harbor, N.Y. 2012), DNA Cloning: A Practical Approach, vol. I & II (D. Glover, ed.); Oligonucleotide Synthesis (N. Gait, ed., 1984); Oligonucleotide Synthesis: Methods and Applications (P. Herdewijn, ed., 2004); Nucleic Acid Hybridization (B. Hames & S. Higgins, eds., 1985); Nucleic Acid Hybridization: Modern Applications (Buzdin and Lukyanov, eds., 2009); Transcription and Translation (B. Hames & S. Higgins, eds., 1984); Animal Cell Culture (R. Freshney, ed., 1986); Freshney, R. I. (2005) Culture of Animal Cells, a Manual of Basic Technique, 5th Ed. Hoboken N.J., John Wiley & Sons; B. Perbal, A Practical Guide to Molecular Cloning (3rd Edition 2010); Farrell, R., RNA Methodologies: A Laboratory Guide for Isolation and Characterization (3rd Edition 2005), Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-3, 4-2), 1855. Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, (2002, Cold Spring Harbor Laboratory, ISBN 0-87969-630-3) provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein, the term "biofilm" includes bacteria, proteins, cells and other materials and organisms that may adhere and aggregate on a surface.

As disclosed herein, cellular interactions with biomedical materials are critical to the performance of medical devices. Biofilm build-up is one major cause of failure for prosthetic implants. Researchers have modified the surface chemistry of biomaterials with biocide-releasing or anti-adhesion coatings, but these are not long-term solutions. There has been increasing interest in designing nanostructured surfaces inspired by nature. In that spirit, the inventors designed nanoscale pillar structures which have the ability to kill bacterial cells purely through physical surface topography. The inventors developed methods that can prevent biofilm buildup through physical surface modifications, demonstrating that a nanostructured surface can kill bacteria upon adhesion without the use of chemical modifications.

In accordance with various embodiments herein, nanostructures were created on polymethylmethacrylate (PMMA) films using nanoimprint lithography, which can involve pressing a silicon mold onto a polymer film at high temperatures above Tg. Softening of polymer films was accomplished by using heated or plasticized films, or by heating the molds. The pillars in this example were made by imprinting 500 nm thick PMMA film at 160 deg. C. twice using line molds where the lines are spaced 416.6 nm apart, and the lines are 208 nm wide. The film was imprinted once, then the mold was rotated by 90 deg., and the film was then imprinted a second time. Nano-pillars with square cross-sections equal to the line width were thus formed. Once imprinted PMMA films were made, the inventors plated *Escherichia coli* on flat and imprinted PMMA films and incubated the samples at 37° C. Bacterial cells were observed using optical microscopy and scanning electron microscopy (SEM). SEM micrographs were obtained without metal coating.

In one embodiment, the present invention provides a method of preparing a bactericidal surface by creating a nanostructure upon an object's surface. In another embodiment, the nanostructure is an imprinted polymer nanostructure. In another embodiment, the nanostructure is created on polymethylmethacrylate (PMMA) film using nanoimprint lithography. In another embodiment, the film is imprinted a first time, followed by rotating by around 90 degrees, followed by imprinting a second time. In another embodiment, the film is imprinted three or more times with varying degrees of rotation. In another embodiment, the nanostructures are pillars made by imprinting PMMA film with lines spaced 200 to 300 nm apart. In another embodiment, the lines are 300 to 400 nm apart. In another embodiment, the lines are 400 to 500 nm apart. In another embodiment, the lines are 500 to 800 nm apart. In another embodiment, the lines are about 400 nm apart. In another embodiment, the lines are 20 to 50 nm wide. In another embodiment, the lines are 50 to 100 nm wide. In another embodiment, the lines are 100 to 200 nm wide. In another embodiment, the lines are 200 to 300 nm wide. In another embodiment, the lines are 300 to 500 nm wide. In another embodiment, the lines are about 200 nm wide. In another embodiment, the bactericidal surface is part of a medical device implant.

As further described herein, using optical microscopy, the inventors were able to see bacterial cells on the surface of both flat and imprinted PMMA films, verifying that there was bacterial adhesion on the samples. With SEM, the inventors observed bacteria morphology and distribution on the different PMMA samples. On the flat PMMA control surface, bacteria were rodshaped, the normal morphology of *E coli*, and randomly distributed on the surface. On nanoline structures, bacteria were also rod-shaped, but most cells were oriented either along or perpendicular to the lines. Some cells along the lines became elongated. On nanopillars, bacteria were randomly dispersed and appear more deflated on the pillars. The inventors noticed that the bacteria conformed roughly to the spacing between pillars and were surrounded by cytoplasm. Many cells have also become quite elongated. The leakage of cytoplasm indicates that nanopillar structures provide bactericidal properties to the PMMA film.

In one embodiment, imprinted polymer nanostructures can guide or prevent bacteria adhesion, and impact the development of implantable devices by providing greater adhesion control by surface nanotexture without chemical modifications to the polymer surface. This will remove the uncertainty of proving long term biocompatibility of a new system or chemical substance and facilitate quick implementation of the device into surgical practice. In accordance with various embodiments herein, these methods and results provide a safe method for surface engineering of biomedical implants.

As further disclosed herein, one cause of failure of implantable medical devices is infection caused by bacteria that adhere to the surface of the implant. Since chemical modifications of the material surface are not long-term solutions in preventing bacterial adhesion, several groups employ physical surface topography made by common microfabrication methods. However, these fabrication methods cannot control the dimensions of very fine-features. Using nanoimprint lithography, the inventors fabricated nanoscale structures, including line gratings and pillars, on the surface of poly(methyl methacrylate) (PMMA) films. Upon seeding *Escherichia coli* on the imprinted PMMA structures, they observed decreased bacterial adhesion and an increase in the percentage of dead cells on the nanopillar structures compared to flat unpatterned surfaces and line gratings. They also observed that the spacing of the features, especially for the pillars, affected the degree of adhesion and increased cell mortality on the imprinted PMMA. These findings demonstrate that varying the dimensions of surface features can affect the mechanism of bacterial adhesion on material surfaces. For example, in one embodiment, the invention provides benefits of utilizing imprinted polymer nanostructures to control adhesion by surface nanotexture without any chemical modifications.

In one embodiment, the present invention provides a medical device with a bactericidal surface where the surface of the device has a polymer surface with imprinted nanostructures. In another embodiment, the medical device is a medical implant.

In one embodiment, the present invention provides a method of preparing an implantable device with antibacterial properties, comprising providing a device and modifying the device to prevent bacteria adhesion by utilizing surface nanotexture without chemical modications to the surface.

In another embodiment, the present invention provides a bactericidal surface, comprising a surface modified by one or more nanostructures. In another embodiment, the nanostructures are imprinted polymer nanostructures. In another embodiment, the nanostructures are created on polymethylmethacrylate (PMMA) film using nanoimprint lithography. In another embodiment, the nanostructures are imprinted a first time, followed by rotating by around 90 degrees, followed by imprinting a second time. In another embodiment, the nanostructures are pillars made by imprinting PMMA film with lines spaced 200 to 300 nm apart. In another embodiment, the nanostructures are pillars made by imprinting lines 20 to 50 nm wide. In another embodiment, the nanostructures are pillars made by imprinting lines 50 to 100 nm wide.

In one embodiment, the present invention provides a method of preventing biofilm formation, comprising providing a polymer film, and creating a plurality of nanostructures upon the polymer film using nanoimprint lithography. In another embodiment, the plurality of nanostructures are nano-pillars. In another embodiment, the nanostructures are imprinted polymer nanostructures.

The present invention is also directed to a kit for preparing a bactericidal surface and/or modifying a device for bactericidal properties. For example, the kit is useful for practicing the inventive method of imprinting nanopillars on a polymer surface. The kit is an assemblage of materials or components, including at least one of the inventive compositions. Thus, for example, in some embodiments the kit contains a composition including materials used for pressing a mold with a negative pattern of interest into a softened polymer film, as described above.

The exact nature of the components configured in the inventive kit depends on its intended purpose. For example, some embodiments are configured for the purpose of preventing and/or treating infection. In one embodiment, the kit is configured particularly for the purpose of treating or administering to mammalian subjects. In another embodiment, the kit is configured particularly for the purpose of treating and/or administering to human subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to create nanopillars on a surface. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

In one embodiment, the specific dimensions of pillar diameter and height are effective for producing various antibacterial properties, and any number of materials may be used. As readily apparent to one of skill in the art, the invention is in no way limited to use of only PMMA or plastic materials. For example, in one embodiment, nanopillars made from materials that are at least as hard as PMMA may be used. In another embodiment, the nanopillars are made of silicon. As readily apparent to one of skill in the art, various embodiments described herein may be used in conjunction with materials and devices like medical devices that are resistant to sterilization procedures, such as higher temperature plastics. For example, in accordance with various embodiments herein, higher temperature plastics used may include polycarbonate (PC), polyetherether ketone (PEEK), or polysulfone (PSu).

One important aspect of our invention is we claim that nanopillars of the dimensions we were able to produce are effective in producing the various antibacterial properties and are not dependent on their being made from PMMA. What is important are the dimensions of pillar diameter and height, and that the pillar materials are at least as hard as PMMA, but can be harder. It's just that plastic pillars are the easiest to produce. Silicon pillars should be equally effective, but are impractical to manufacture. Therefore the embodiment of our invention has been in a typical plastic such as PMMA. Higher temperature plastics that are more resistant to repeated sterilization procedures, such as those used in medical devices, should also be included in this invention. Such plastics include polycarbonate (PC), polyetherether ketone (PEEK), polysulfone (PSu), etc.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Cellular interactions with biomedical materials are critical to the performance of medical devices. Biofilm build-up is one major cause of failure for prosthetic implants. Researchers have modified the surface chemistry of biomaterials with biocide-releasing or anti-adhesion coatings, but these are not long-term solutions. There has been increasing interest in designing nanostructured surfaces inspired by nature. The inventors designed nanoscale pillar structures which have the ability to kill bacterial cells purely through physical surface topography. The inventors developed methods that can prevent biofilm buildup through physical surface modifications.

Nano structures were created on polymethylmethacrylate (PMMA) films using nanoimprint lithography, which involves pressing a silicon mold onto a polymer film at high temperatures above Tg. Softening of polymer films was accomplished by using heated or plasticized films, or by heating the molds. The pillars in this example were made by imprinting 500 nm thick PMMA film at 160 deg. C. twice using line molds where the lines are spaced 416.6 nm apart, and the lines are 208 nm wide. The film was imprinted once, then the mold was rotated by 90 deg., and the film was then imprinted a second time. Nano-pillars with square cross-sections equal to the line width were thus formed. Once imprinted PMMA films were made, the inventors plated *Escherichia coli* on flat and imprinted PMMA films and incubated the samples at 37° C. Bacterial cells were observed using optical microscopy and scanning electron microscopy (SEM). SEM micrographs were obtained without metal coating.

Using optical microscopy, the inventors were able to see bacterial cells on the surface of both flat and imprinted PMMA films, verifying that there was bacterial adhesion on the samples. With SEM, the inventors observed bacteria morphology and distribution on the different PMMA samples. On the flat PMMA control surface, bacteria were rodshaped, the normal morphology of *E coli*, and randomly distributed on the surface. On nanoline structures, bacteria were also rod-shaped, but most cells were oriented either along or perpendicular to the lines. Some cells along the lines became elongated. On nanopillars, bacteria were randomly dispersed and appear more deflated on the pillars. The inventors noticed that the bacteria conformed roughly to the spacing between pillars and were surrounded by cytoplasm. Many cells have also become quite elongated. The leakage of cytoplasm indicates that nanopillar structures provide bactericidal properties to the PMMA film.

In conclusion, imprinted polymer nanostructures can guide or prevent bacteria adhesion and impact the development of implantable devices by providing greater adhesion control by surface nanotexture without chemical modifications to the polymer surface. This will remove the uncertainty of proving long term biocompatibility of a new system or chemical substance and facilitate quick implementation of the device into surgical practice. These methods and results provide a safe method for surface engineering of biomedical implants.

Example 2

Length Measurements of Bacteria

The length and diameter of bacterial cells in randomly chosen regions in the micrographs were measured to determine cell aspect ratios on the flat control and the nanopatterned surfaces. The nanopatterned surfaces used for these experiments were line gratings L1, the smaller spaced lines, and round pillars P1, the smaller spaced pillars. The cell aspect ratio was calculated as the ratio of the length over the diameter of the bacterial cells. The average aspect ratio of bacterial cells on the flat PMMA control, line gratings L1 and round pillars P1 were determined across three trials. The average aspect ratios of the live and dead bacterial cells on the flat PMMA control across three trials were 2.34 and 3.41, respectively. The average aspect ratios of the live and dead bacterial cells on line gratings L1 across three trials were 2.02 and 3.42, respectively. The average aspect ratios of the live and dead bacterial cells on the round pillared PMMA P1 across three trials were 2.77 and 3.48, respectively.

Figure 5:
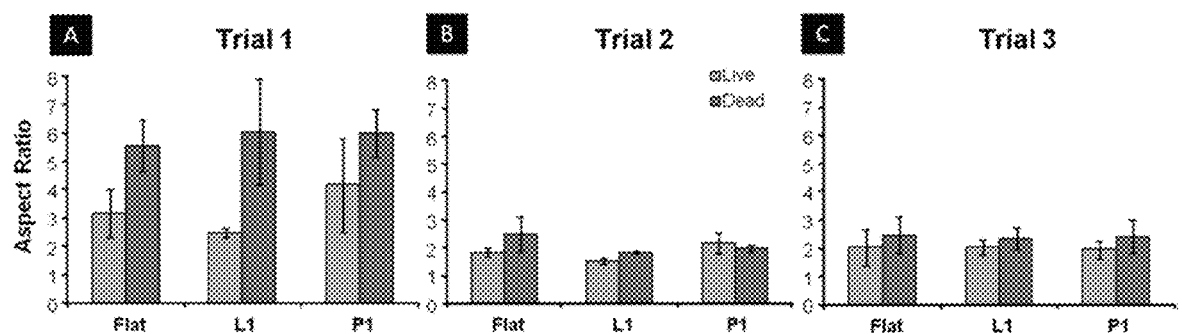
FIG. 5 depicts, in accordance with various embodiments of the present invention, bacterial cell aspect ratios on nanopatterned surfaces. The average aspect ratio of the live and dead cells on the flat PMMA control, line gratings L1, and round pillars P1 are shown for each of the three experimental trials: (A) trial 1, (B) trial 2, (C) trial 3. The aspect ratio is the length of the cell divided by the diameter of the cell. The length and diameter of bacterial cells in randomly chosen regions on the micrographs were measured to determine cell aspect ratios on the nanopatterned surfaces. The data show that the dead cells are longer than the live cells regardless of the nanopatterns. Cell aspect ratios are shown as mean±standard deviation. Green bars indicate live cells while red bars indicate dead cells.
Figure 6:
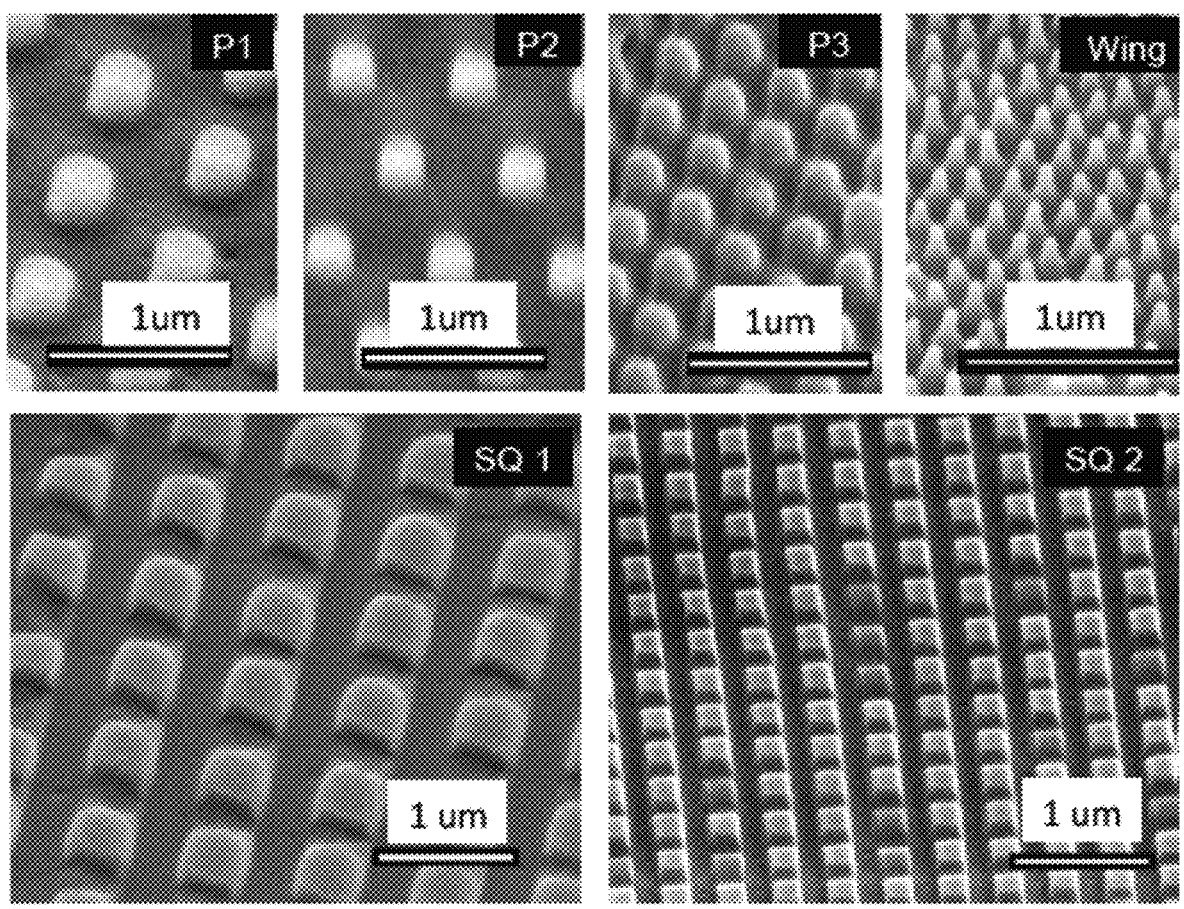
FIG. 6 depicts, in accordance with various embodiments of the present invention, scanning electron micrographs (SEM) images of library of pillared surfaces.
Figure 7:
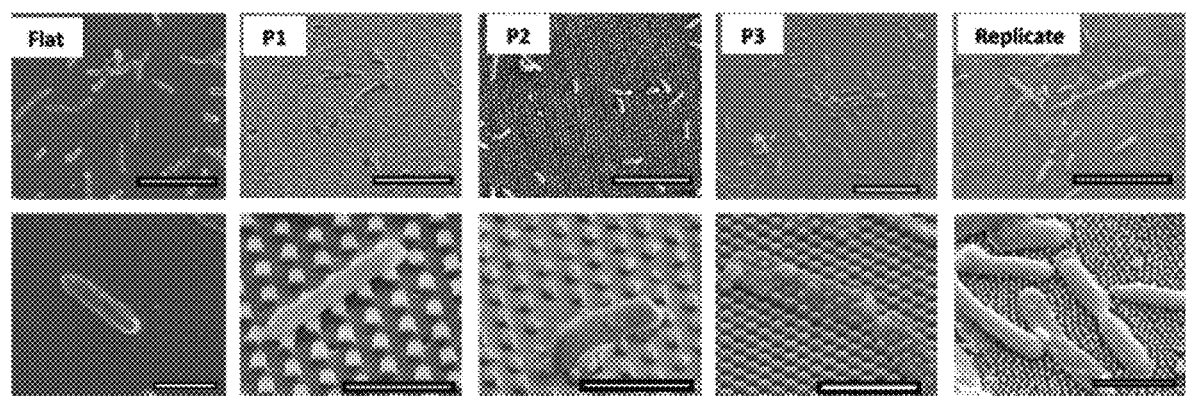
FIG. 7 depicts, in accordance with various embodiments of the present invention, a comparison of bacteria on flat and imprinted PMMA films. Bacteria on flat surface were fully rod-shaped while the bacteria on nanopillars appear deflated. In addition, elongated and oriented cells were observed on nanopillared surfaces. Top row scale=10 um; Bottom row scale=2 um.
Figure 8:
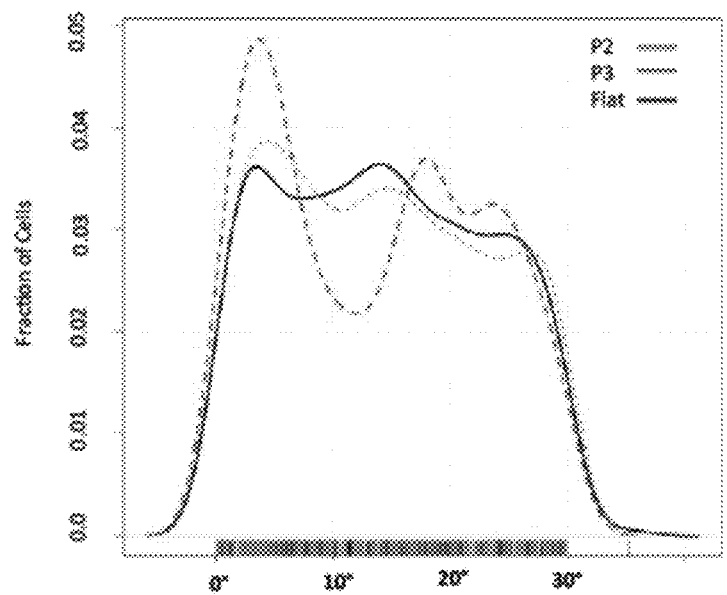
FIG. 8 depicts, in accordance with various embodiments of the present invention, quantitative analysis of (A) bacterial orientations with respect to rows of pillars (B) bacterial cell lengths. Orientation to pillar rows is shown to be pillar geometry dependent. *E. coli* length is affected by pillared films.
Figure 8:
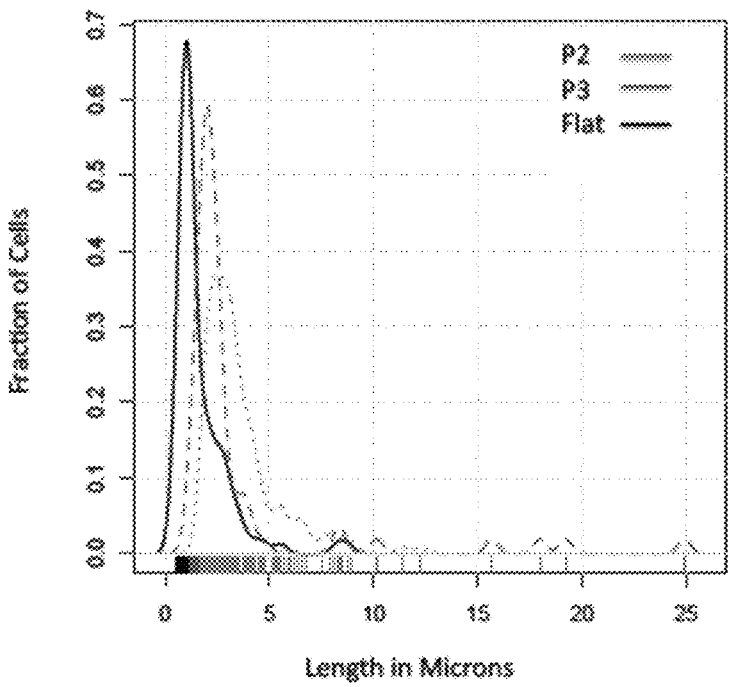
Figure 9:
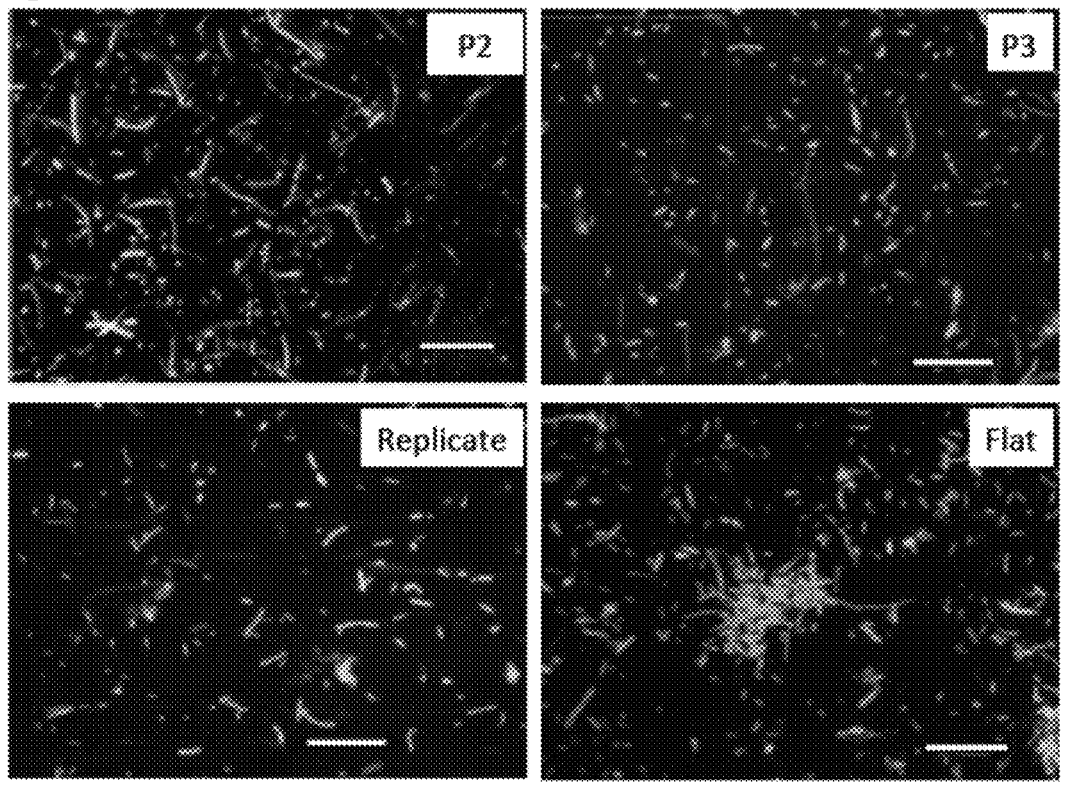
FIG. 9 depicts, in accordance with various embodiments of the present invention, fluorescence microscopy viability study. Cells tagged with red are dead. Cells tagged with green are live. Scale bar=30 um.
Figure 10:
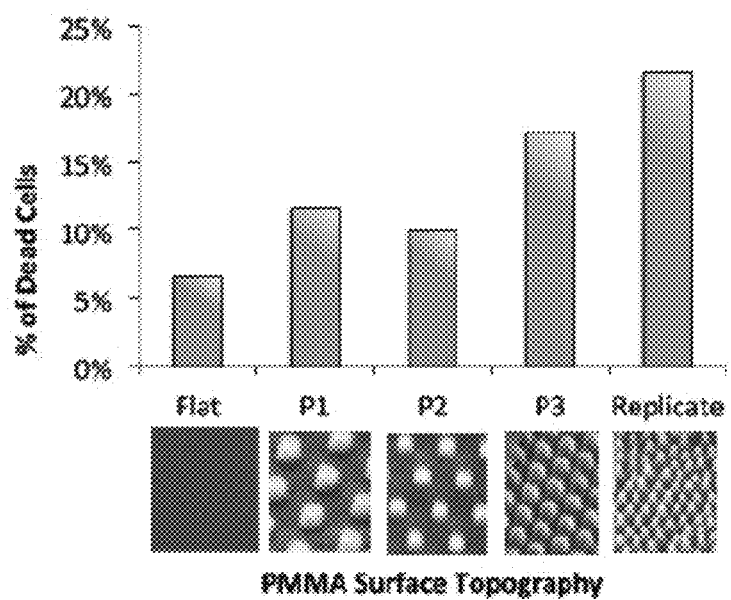
FIG. 10 depicts, in accordance with various embodiments of the present invention, percentage of dead cells increases on pillared films compared to flat films. Films with smaller, closer spaced pillars have higher percentages of dead cells.
Figure 11:
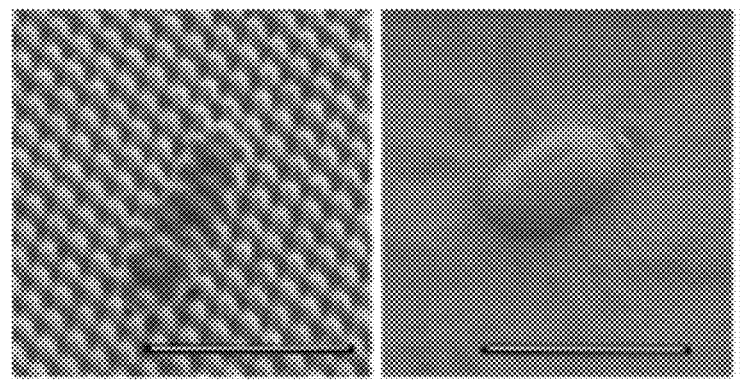
FIG. 11 depicts, in accordance with various embodiments of the present invention, *E. coli* bacterium interacting with PMMA film. On the left, *E. coli* bacterium interacting with a nanoimprinted PMMA film. The cell appears deflated, with pillars protruding through. On the right, *E. coli* bacterium interacting with flat PMMA. The cell appears fully rod shaped and adherent to the surface. Scale=2 microns.

The data shows that length is not consistently indicative of the viability of the bacteria nor is the length always affected by the nanostructures of the surface. They did observe that the aspect ratio of the dead cells appear to be greater than the aspect ratio of the live cells regardless of the surface pattern. As shown in FIG. 5 herein, results depict the average aspect ratios for the live and dead cells on the surface patterns for each experimental trial.

Example 3

Overview

One cause of failure of implantable medical devices is infection caused by bacteria that adhere to the surface of the implant. Since chemical modifications of the material surface are not long-term solutions in preventing bacterial adhesion, several groups employ physical surface topography made by common microfabrication methods. However, these fabrication methods cannot control the dimensions of very fine-features, especially at the nanoscale. Using nanoimprint lithography, they fabricated nanoscale structures, including line gratings and pillars, on the surface of poly (methyl methacrylate) (PMMA) films. Upon seeding *Escherichia coli* on the imprinted PMMA structures, they observed decreased bacterial adhesion and an increase in the percentage of dead cells on the nanopillar structures compared to flat unpatterned surfaces and line gratings. They also observed that the spacing of the features, especially for the pillars, affected the degree of adhesion and increased cell mortality on the imprinted PMMA. The findings suggest that varying the dimensions of surface features can affect the mechanism of bacterial adhesion on material surfaces. This work demonstrates that imprinted polymer nanostructures may be utilized to control adhesion by surface nanotexture without any chemical modifications.

Example 4

Results

Reproducibility of Nanoimprinted Structures:

Imprinted PMMA samples were first examined under SEM to assess how successful nanoimprinting was in creating the structures on the PMMA surface (FIG. 1 herein). Before examination, PMMA samples were coated with a 1-2 nm layer of iridium. Dimensional measurements from SEM micrographs were performed using the measurement tool in the SEM software and ImageJ. Structures could be viewed at a horizontal field width as low as 2.98 μm to measure the dimensions of lines and pillars structures of the first and last samples. Dimensions of the imprinted patterns and the pattern's respective stamp are listed in Table 1 below.

TABLE 1

Measured dimensions of Nanoimprinted Features

|  | Imprint Dimensions (nm) | Mold Dimensions (nm) |
|---|---|---|
| Line gratings L1 | width: 134 ± 8<br>periodicity: 272 ± 9 | width: 144 ± 4<br>periodicity: 282 ± 6 |
| Line gratings L2 | width: 225 ± 10<br>periodicity: 411 ± 16 | width: 211<br>periodicity: 411 |
| Round pillars P1 | diameter: 215 ± 23<br>periodicity: 595 | diameter: 203 ± 14<br>periodicity: 600 |
| Round pillars P2 | diameter: 267 ± 11<br>periodicity: 692 ± 24 | diameter: 272 ± 9<br>periodicity: 697 ± 5 |

It was found that the line width and periodicity of both imprinted line gratings were similar to the width and periodicity of the silicon stamp gratings. Likewise, it was found that the diameter and periodicity of both imprinted round pillar structures were similar to those of the respective negative silicon mold containing nanoholes. Decrease in dimension is possibly due to thermal shrinkage during the cooling process. In addition, the image contrast of the edges may cause the holes and trenches in the molds to appear smaller and the pillars and line gratings larger. However, given this uncertainty, the imprinted structures appear to be faithful reproductions of the molds (FIG. 1). This indicates that nanoimprint lithography is a reliable technique for reproducing structures of approximately the same dimensions as the mold features. Fabrication of the square pillars was challenging in that we had to make sure that the lines from the first step did not melt during the second imprinting step. They succeeded in imprinting square pillars with side lengths of approximately 200 nm and a periodicity of approximately 420 nm (FIG. 1H).

Figure 2:
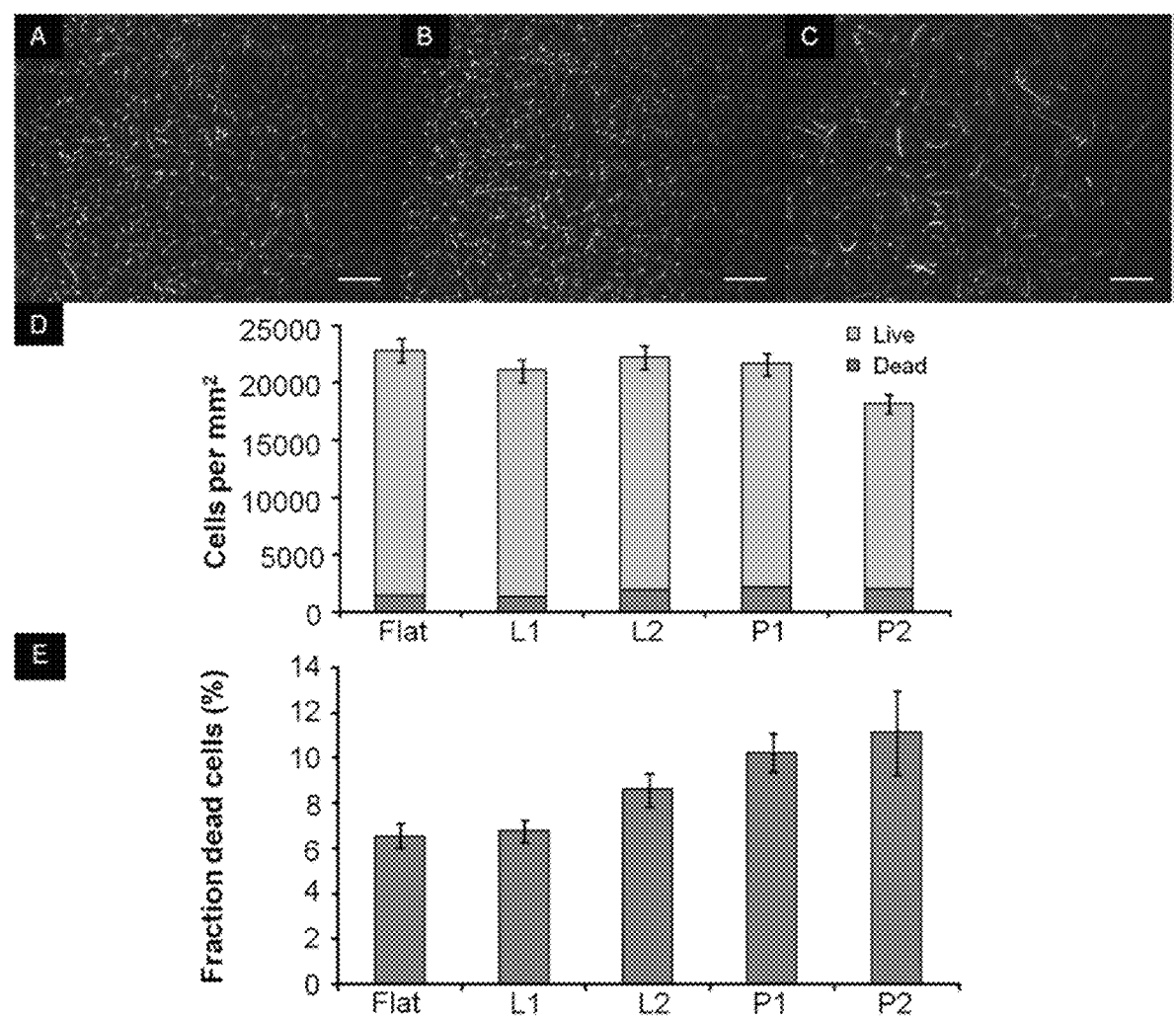
FIG. 2 depicts, in accordance with various embodiments of the present invention, fraction of dead cells on imprinted surfaces. Live-dead assay micrographs are representative micrographs on the flat control (A), line pattern L1 (B) and pillar pattern P1 (C). Green fluorescent cells are stained with SYTO9, which stains all bacterial nucleic acids, while red fluorescent cells are stained with propidium iodide, which stains the nucleic acids of damaged cells. The number of red cells, which indicate dead cells, is greater on the pillared pattern compared to the number on the flat film and line gratings. The total number of cells (live cells+dead cells) on the pillared surfaces, especially on the P2 pattern, is less than the total number of cells on the flat control. Total cell count (D) depicts mean±uncertainty error due to image processing. The fraction of dead cells, calculated as the ratio of the number of dead cells over total number of cells, was significantly greater on the pillared surfaces compared to the flat control and line gratings. Dead cell fraction (E) depicts mean±standard error of the mean. (A-C) Scale bars=30 µm.

Bacterial Cell Viability on Nanoimprinted Surfaces:

In this series of observations, they first took optical microscope images of the bacteria after 20 hours of incubation. For Flat, L1 and P1, three experimental trials were run. For L2 and P2, two experimental trials were run. They observed bacterial cells on the surface of both flat and imprinted PMMA samples, verifying that bacteria adhered to the surface of PMMA, regardless of the presence of the nanostructures. From the optical micrographs (area=0.542 sq. mm), there were, on average, $2.280 \times 10^4$ cells/mm2 on the flat PMMA control (n=9), $2.102 \times 10^4$ cells/mm2 on the line gratings of PMMA L1 (n=10), $2.225 \times 10^4$ cells/mm2 on line gratings of PMMA L2 (n=8), $2.163 \times 10^4$ cells/mm2 on pillared PMMA P1 (n=17) and $1.813 \times 10^4$ cells/mm2 on pillared PMMA P2 (n=8) (Table 2). There were fewer cells adhering to the pillar surface, especially on P2 (FIG. 2D).

TABLE 2

Total Cell Count on Patterned Surfaces

| Surface Pattern | Total Cell Count (cells/mm$^2$) | Dead Cell Count (cells/mm$^2$) |
|---|---|---|
| Flat film (n = 9) | 22801 | 1489 |
| Line gratings L1 (n = 10) | 21022 | 1388 |
| Line gratings L2 (n = 8) | 22247 | 1893 |
| Round Pillars P1 (n = 17) | 21629 | 2163 |
| Round Pillars P2 (n = 8) | 18130 | 2093 |

Next, they performed a live-dead assay by staining the cells as described in the methods section in order to assess the efficacy of the imprinted nanostructures in killing bacterial cells on those surfaces. After fluorescence microscopy, Image J was used to calculate the percentage of dead cells on each surface type (FIG. 2A-C). The number of cells stained by propidium iodide in each TRITC-filtered image, to get the dead cell count, was divided by the number of cells in the corresponding bright field image, to obtain the total cell count, in order to calculate the fraction of dead cells on the patterned surfaces. They found that after 20 hours, on average, the number of dead cells was 1489 cells/mm2 on flat PMMA, 1388 cells/mm2 on L1, 1893 cells/mm2 on L2, 2163 cells/mm2 on P1, and 2093 cells/mm2 on P2 (Table 2). Upon examining images pooled from three different trials, they observed a 45 percent increase in the number of dead cells on the pillar surface compared to the flat control. The average percentage of dead cells was 6.6% on the flat PMMA control, 6.8% on line gratings L1, 8.6% on line gratings L2, 10.3% on pillars P1 ($p<0.05$ compared to flat), and 11.1% on pillars P2 ($p<0.05$ compared to flat) (FIG. 2E). There was some variability in the percentage of dead cells between the three different trials, however, whose individual percentages on pillared films were 15%, 9% and 10% compared with 7%, 5%, and 8% on the flat films.

Figure 3:
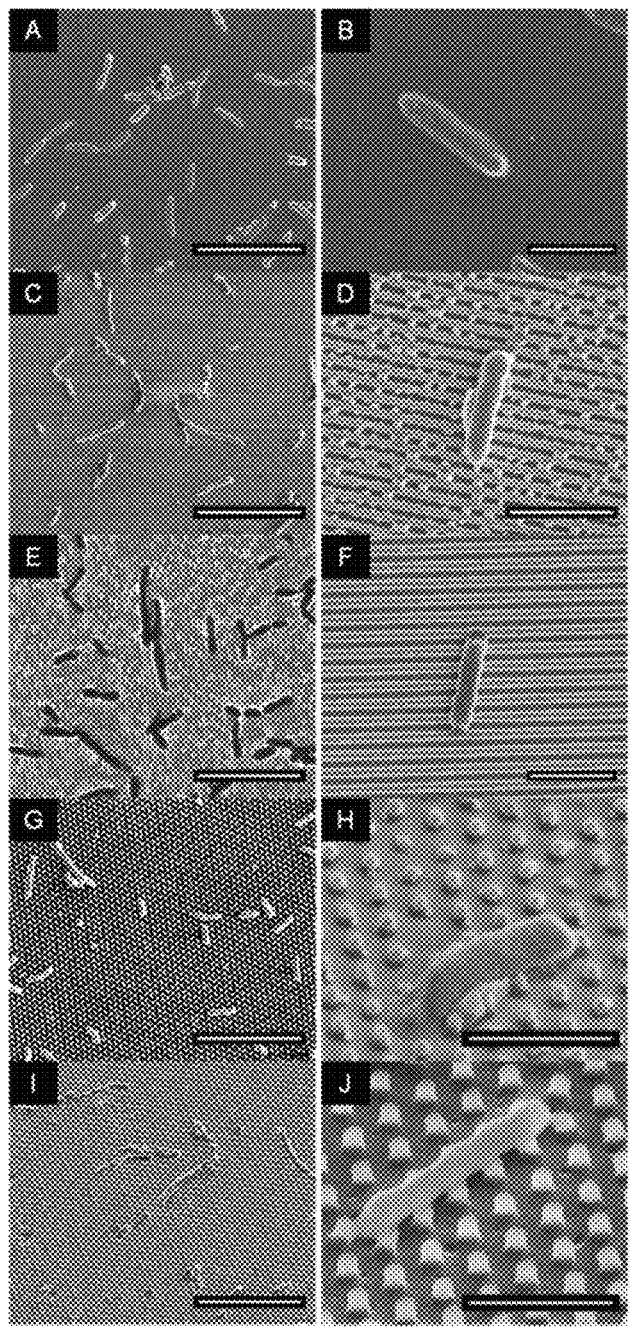
FIG. 3 depicts, in accordance with various embodiments of the present invention, SEM micrographs of bacteria on patterned PMMA surfaces. Images in the left column are at 5000×. In the right column, images B, D, and F are at 20000×, and images H and J are at 35000×. The morphology and spread of bacterial cells were observed on flat control (A, B), line gratings L1 (C, D), line gratings L2 (E, F), round pillars P1 (G, H), and round pillars P2 (I, J). While the bacteria remain rod-shaped on the flat PMMA and line gratings, the bacteria on the pillars drape across several pillars, at times partly overhanging at the edge of a pillar, as observed on both P1 and P2 pillars (H and J, respectively). There is evidence of leakage of cytoplasm in H. Images E and J were imaged at 5 kV. All other micrographs were imaged at 2 kV. Scale bars in left column=10 µm. Scale bars in right column=2 µm.
Figure 4:
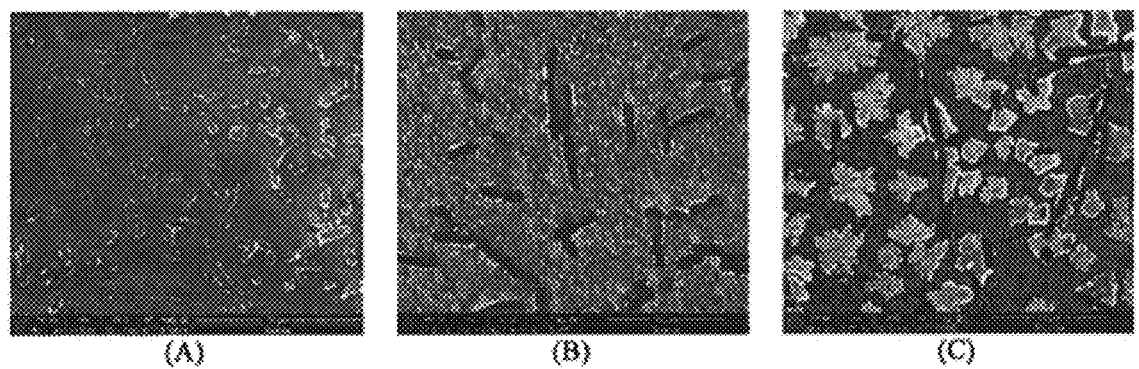
FIG. 4 depicts, in accordance with various embodiments of the present invention, comparison of bacteria on flat and imprinted PMMA films. Bacteria on flat (A) and nanolines (B) were fully rod shaped while the bacteria on nanopillars (C) appear deflated while leaked cytoplasm surrounded the cells.

Bacterial Response to Nanoimprinted Surfaces:

The inventors examined the morphology and distribution of bacterial cells on the flat and imprinted PMMA samples using SEM. Bacterial cells were fixed with 2.5% glutaraldehyde for one hour in these experiments. On the flat PMMA control surface, bacteria were rod-shaped, the normal morphology of *E. coli* cells (FIG. 3A, B). On the nanoline gratings, bacterial cells were also rod-shaped on both L1 (FIG. 3C, D) and L2 (FIG. 3E, F), but on nanopillar structures, bacteria appeared more deflated, stretched over several pillars on P1 (FIG. 3G, H) and P2 (FIG. 3I, J). They additionally observed that on both L1 and L2 line gratings, the bacteria appear to favor a biaxial orientation either parallel to or perpendicular to the lines. Upon pillars, bacteria appear to conform roughly to the spacing between pillars on both P1 and P2 patterns.

Some bacterial cells, especially those on pillared surfaces appear more elongated than a typical *E. coli* cell, which are 2 μm long and 0.5 μm wide. They measured the lengths and diameters of live and dead cells in randomly chosen regions of the fluorescence micrographs of the flat PMMA control, line gratings L1 and pillared PMMA P1. They also calculated the aspect ratio (length/diameter) of those same cells. Cells that appeared to be in the process of dividing were not included for calculations. The average aspect ratios of the live and dead bacterial cells on the flat PMMA control across three trials were 2.34 and 3.41, respectively. The average aspect ratios of the live and dead bacterial cells on line gratings L1 across three trials were 2.02 and 3.42, respectively. The average aspect ratios of the live and dead bacterial cells on the round pillared PMMA P1 across three trials were 2.77 and 3.48, respectively. These data show that length is not consistently indicative of the viability of the bacteria nor is the length always affected by the nanostructures of the surface.

The inventors successfully fabricated nanoscale structures on the surface of the PMMA films, and produced nanopillars that mimic those found on the wings of many insects. They found that varying the dimensions of surface features affects bacterial behavior, such as growth and viability, as well as the mechanism of bacterial adhesion on material surfaces. More importantly, they illustrated the benefits of using imprinted polymer nanostructures to guide or prevent bacteria adhesion by precisely controlling their geometry and dimensions on the nm scale. Using surface nanotexture greatly benefits the development of implantable devices by providing greater adhesion control without any chemical modifications. This removes the burden of proving long-term biocompatibility and can facilitate the implementation of the device into surgical practice. Results from this study provide a safe and effective method for surface engineering of biomedical implants.

Example 5

Methods

Fabrication of Nanostructures on Polymer Surface:

Nanostructures were fabricated from poly(methyl methacrylate) (PMMA), a polymer approved by the FDA for use in biomedical implants. PMMA solution in toluene (5% by weight) was spin-coated on piranha-cleaned glass cover slips (22×22 mm) at 600 rpm for 45 seconds to create a flat PMMA coating and then dried on a hot plate at 100° C. Silicon nanoline and nanohole molds (Lightsmyth, 12.5× 12.5 mm and 8×8.3 mm, respectively) were used for imprinting desired structures on the PMMA film. After cleaning the silicon molds with piranha solution (3:1 sulfuric acid: hydrogen peroxide), an anti-stiction coating, specifically perfluorodecyltrichlorosilane (Gelest, Inc.), was applied to the mold by molecular vapor deposition. Nanostructures were made on the polymer surface via nanoimprint lithography. Inside the nanoimprinter (Jenoptik, Hex03), the polymer film is heated to 160° C., which is 50° C. above the glass transition temperature of the polymer, and the silanized silicon mold is pressed down against the polymer film with a force of 400 N for 5-10 minutes. The mold was then allowed to cool to 50° C. in the time span of 2.5 minutes. The glass-supported PMMA film was released from the silicon mold, leaving the nanostructures on the film surface. This process was used to fabricate the nanolines and the round nanopillars. To fabricate the square pillars, the inventors double-imprinted a line grating pattern using the lines molds (FIG. 1G), creating a grid pattern on the polymer surface. To make sure the first imprint did not lose its shape during the second imprinting step, the temperature of the second imprinting was 20° C. lower than that in the first. All nanoimprinted surfaces were examined using scanning electron microscopy (SEM). Images were taken at 5 kV using the FEI Quanta 3D at the Laboratory for Electron and X-ray Instrumentation (LEXI) at UC Irvine at varying magnifications.

Bacteria Culture and Experiments:

For each trial, DH5-alpha gram negative *Escherichia coli* were used to examine antibacterial properties of the PMMA films, both with and without the nanostructures. A glycerol stock solution of *E. coli* was inoculated in 5 ml Luria Broth (LB) media overnight in an air bath shaker at 300 rpm in 37° C. The bacteria solution was diluted 1000 times in LB. 10 μl of this diluted solution was added on an LB-agar plate and was spread on the agar using a sterile metal loop and a turntable per the spread plate method. The plate was incubated at 37° C. overnight. At the start of each experiment, fresh starter cultures were grown overnight at 37° C. in 5 ml LB media by shaking at 200 rpm. Bacterial suspensions were adjusted to OD600=0.3. Each PMMA sample was immersed in 2 ml of this bacteria suspension and incubated for 20 hours at 37° C. PMMA samples were washed twice with 1×PBS at room temperature (25° C.) prior to conducting experiments. For bacteria experiments, they did not seed cells on the square pillared surfaces.

To examine morphology changes, bacterial cells were fixed with 2.5% glutaraldehyde and examined using optical microscopy and SEM (FEI Quanta 3D). For viability experiments, unfixed samples were incubated for 15 minutes with the BacLight™ Live/Dead solution (Molecular Probes, Life Technologies, Carlsbad, Calif.) dissolved in PBS at the concentration recommended by the manufacturer. Samples were rinsed twice with PBS and examined under fluorescence (Nikon TS 100 inverted microscope) using FITC filter to view live cells and TRITC filter to view dead cells.

Statistical Analysis:

Statistical significance for cell count and viability was determined using the Student's t-test assuming unequal variance. All micrographs were analyzed using ImageJ (NIH, version 1.47) to determine cell count. For each trial, cell counts were measured for 3 to 8 windows of 0.542 mm2 at each condition. Thus, between 8 and 17 total windows were counted for each condition. Viability of cells was determined by taking the ratio of the dead cell count over the total cell count. The standard error for cell count analysis is due to the 5% error associated with image processing. Standard deviation was calculated for the fraction of dead cells.

Example 6

Imprinted Polymer Nanostructures to Guide Bacteria Adhesion and Kill Bacteria that do Adhere Though bacterial biofilms are ubiquitous in nature, they are often detrimental in industrial settings, such as water distribution systems. They can even be fatal, as in the case of biofilms that form on implanted medical devices. Researchers have developed surfaces with biocide-releasing or anti-adhesion chemical coatings, but cannot serve as long-term solutions. Higher-order organisms have evolved to cope with biofilm build up, such as nanoscale pillar structures on the cicada wing surface which have the ability to kill bacterial cells purely through physical surface topography. The inventors developed methods that can prevent biofilm buildup through physical surface modifications with some similarities to structures found in nature.

Methods:

The inventors created nanostructures on polymethylmethacrylate (PMMA) films using nanoimprint lithography, which involves pressing a silicon mold with a negative of the pattern of interest into a polymer film at high temperatures above the glass transition temperature (Tg). Softening of polymer films was accomplished by using heated or plasticized films, or by heating the molds. First, arrays of pillars with circular cross sections were fabricated. In one instance, nanopillars on the cicada's wing were imprinted in a 2-step process. They used soft lithography to make a negative mold from hardened polydimethylsiloxane (PDMS) for use in the imprinting process. In another instance, a nickel mold was used to print pillars with ~320 nm periodicity and ~190 nm in diameter (P3). Two silicon molds were also used to fabricate pillar arrays with 595 nm periodicity and 215 nm width pillars (P2), and with 692 nm periodicity and 267 nm diameter (P1). These molds were imprinted into a spin-coated PMMA on glass (500 nm) at 170° C. and 2 MPa. Next, pillars with square crosssections (SQ1, SQ2) were fabricated. The pillars in this example were made by imprinting 500 nm thick PMMA film at 160 deg. C. twice using line molds. Two line molds were used: 208 nm width lines (SQ2) and 442 nm width lines (SQ1). The film was imprinted once, then the mold was rotated by 90 deg., and the film was then imprinted a second time. Nano-pillars with square cross-sections equal to the line width were thus formed. Scanning electron micrographs are depicted herein and a table of all pillar dimensions are shown below.

TABLE 3

Table of important dimensions of pillared surfaces.

|  | Width | Height | Period |
| --- | --- | --- | --- |
| P1 | 267 nm | ~300 nm | 692 nm |
| P2 | 215 nm | ~300 nm | 595 nm |
| P3 | 190 nm | ~350 nm | 320 nm |
| Wing Replicates | Cap: 60 nm Base: 120 nm | 200 nm | 170 nm |
| SQ1 | 442 nm | ~300 nm | 848 nm |
| SQ2 | 139 nm | ~300 nm | 278 nm |

After imprinting the PMMA films, the inventors plated *Escherichia coli* (*E. coli*) on flat and imprinted PMMA films and incubated the samples at 37° C. Bacterial cells were observed using optical microscopy, atomic force microscopy and scanning electron microscopy (SEM). Additionally, a viability staining procedure was performed. This staining solution consists of two fluorescence dyes: propidium iodide can only permeate into membrane-compromised cells (red indicates dead cells), and SYTO9 can permeate into any cell (green indicates live cells). These samples were then imaged using wide-field fluorescence microscopy to ascertain the viability of cells on the flat and pillared surfaces.

Results:

Using optical microscopy, they were able to see bacterial cells on the surface of both flat and imprinted PMMA films, verifying that there was bacterial adhesion on the samples. With SEM, they observed bacteria morphology and distribution on the different PMMA samples. On the flat PMMA control surface, bacteria were rod-shaped, the normal morphology of *E. coli*, and randomly distributed on the surface. On nanopillars, bacteria appear deflated, indicating a loss of turgor indicative of cell death. In some cases, cytoplasm can be seen leaking out of the cells as well. Additionally, bacterial orientations seem to be geometry dependent, with wider spaced pillars (P1, P2)) causing bacteria to conform roughly to the spacing between pillars. Many cells have also become quite elongated.

In a quantitative orientation analysis for several of the circular cross-section pillars, the inventors first observed that bacteria orient along the lines of pillars or at a 30° to a line of nearest-neighbor pillars on pillars with wider spacing. On flat films and films with very closely spaced pillars, there was no preferential orientation measured. Therefore, bacteria on wider-spaced pillar arrays may be able to orient such that they can avoid penetration by pillars. This indicates that there is a threshold for pillar spacing, above which the efficacy of the surface patterns will be diminished. Quantitative analysis of elongation of bacteria on circular cross section pillars confirms the visual observations that bacteria on pillared films elongate along the lines.

Elongation or filamentation of *E. coli* bacteria is indicative of stress, as exhibited by cells that cannot divide normally.

Representative images depicted herein from the viability study on circular cross-section pillars show more red, or dead bacteria on the pillared films than on the flat films. These results were quantified by calculating the percentage of cells on the surface that were dead. The plots show a higher percentage of dead bacteria on the smaller, closer spaced pillars; the cicada wing replicate had the highest percentage of the pillared surfaces. All pillared films have a higher percentage of dead cells than on flat films.

Conclusions:

The inventors illustrated the ability of imprinted polymer nanostructures to guide bacteria adhesion and kill bacteria that do adhere. This nanotexture functions without chemical modifications to the polymer surface. This removes the uncertainty of proving long-term stability and efficacy of a chemical antimicrobial substance, facilitating quick implementation of the texture on medical devices and environmental surfaces. Results provide a safe method for generating antibacterial surfaces on consumer polymer surfaces.

Example 7

Scalable Biomimetic Antibacterial Coating

It has been found that the nanopillars on cicada wings are inherently antibacterial, irrespective of surface chemistry. Thus, fabrication of devices presenting such nanostructures would obviate the requirement for any special surface chemical modification. Other nano- and microstructured antibacterial surfaces proposed include drawbacks such as failure to perform in an aqueous environment, incompatibility with ordinary polymer surfaces, and scale-up difficulties.

The inventors applied industrial nano structuring techniques to generate cicada-wing like nanostructures on the surfaces of a polymer often used in biomedical devices: poly(methylmethacrylate) (PMMA). To begin, they replicated the nanopillars of a cicada wing utilizing a double imprinting process. First they replicated the pillars in hard polydimethylsiloxane (hPDMS) and applied a support layer of PDMS to produce pliable elastomeric stamps presenting large areas (diameter 15 mm) of nanoholes. Next, they utilized either dropcasting of polymer solution or thermal imprinting into a polymer thin film to generate fields of polymer pillars. Dropcasting was used for experiments that required a large area of pillars, since the natural curvature of the cicada's wing precludes large-area thermal imprinting into flat polymer thinfilms. In contrast, thermal imprinting generated smaller areas of very flat, thin, pillared polymer films, which were more suitable for light transmission microscopy. Films were characterized using scanning electron microscopy (SEM) and atomic force microscopy (AFM). To make the nanopatterning technique more industrially viable and generate a larger patterned area, they utilized nanoimprint lithography. A commercially available antireflective stamp (Holotools, Germany) with a nanopillared pattern similar to that of the cicada's wing was used to imprint large, flat, nanostructured polymer thin films.

In contaminated aqueous environments, the nanopillared surfaces 1) killed surface-adherent *E. coli*, as determined by a standard fluorescence based viability assay (Baclight, Invitrogen); and 2) decreased bacterial load in the aqueous environment, as evidenced by a decrease in colony forming units in suspension over time (up to 24 hours) when compared with flat controls. These surfaces could be used for a wide variety of environmental and medical applications, including surgical trays/instruments and door handles (which function in air), and for implantable medical devices or catheter tubes (which function in aqueous environments).

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A bactericidal substrate characterized by an ability to kill target bacteria upon adhesion to its surface, comprising:
   a substrate having a bactericidal surface modified by a pattern comprising a plurality of uniform nanopillars evenly spaced by a plurality of uniform spacings, wherein
      the plurality of uniform nanopillars is characterized by a nanopillar width and a nanopillar periodicity, and
      the plurality of uniform spacings is characterized by a spacing width, wherein
         the spacing width is a width of a gap between any two adjacent nanopillars as measured at their top edges, and
         the nanopillar periodicity is a sum of the nanopillar width and the spacing width, and wherein
      the nanopillar width and the spacing width are, each, smaller than a width of the target bacteria, wherein the width of the target bacteria is the smallest dimension of the target bacteria, and wherein
      the nanopillar width, the nanopillar periodicity, and the spacing width are adjustable manufacturing parameters, wherein
      the pattern is configured such that contact by the target bacteria with the top edges of one or more of the plurality of uniform nanopillars immobilizes the target bacteria and causes death of the target bacteria, and wherein
the bactericidal surface is characterized by a surface area, and
the plurality of uniform nanopillars comprises a hard plastic characterized by a modulus of at least 10 MPa.

2. The bactericidal substrate of claim 1, wherein the spacing width is 10 to 500 nm.

3. The bactericidal substrate of claim 1, wherein the spacing width is 300 nm or less.

4. The bactericidal substrate of claim 1, wherein the spacing widths is 700 nm or less.

5. The bactericidal substrate of claim 1, wherein the nanopillar width is 25 to 500 nm.

6. The bactericidal substrate of claim 1, wherein the nanopillar width is 700 nm or less.

7. The bactericidal substrate of claim 1, wherein the nanopillar width is 100 nm or less.

8. The bactericidal substrate of claim 1, wherein the nanopillar width is 30 nm or less.

9. The bactericidal substrate of claim 1, wherein the plurality of uniform nanopillars comprises nanopillars with a circular cross section.

10. The bactericidal substrate of claim 1, wherein the hard plastic is a polymethylmethacrylate.

11. The bactericidal substrate of claim 1, wherein the hard plastic is selected from the group consisting of: polycarbonate, polystyrene, polyetherether ketone, or polysulfone.

12. The bactericidal substrate of claim 1, wherein the hard plastic is resistant to repeated sterilization procedures.

13. A medical device, comprising
   a bactericidal substrate characterized by an ability to kill target bacteria upon adhesion to its surface, comprising:
      a substrate having a bactericidal surface modified by a pattern comprising a plurality of uniform nanopillars evenly spaced by a plurality of uniform spacings, wherein
         the plurality of uniform nanopillars is characterized by a nanopillar width and a nanopillar periodicity, and
         the plurality of uniform spacings is characterized by a spacing width, wherein
            the spacing width is a width of a gap between any two adjacent nanopillars as measured at their top edges, and
            the nanopillar periodicity is a sum of the nanopillar width and the spacing width, and wherein
         the nanopillar width and the spacing width are each smaller than a width of the target bacteria, wherein the width of the target bacteria is the smallest dimension of the target bacteria, and wherein
         the nanopillar width, the nanopillar periodicity, and the spacing width are adjustable surface manufacturing parameters, wherein
         the pattern is configured such that contact by the target bacteria with the top edges of one or more of the plurality of uniform nanopillars immobilizes the target bacteria and causes death of the target bacteria, and wherein
      the bactericidal surface is characterized by a surface area, and
      the plurality of uniform nanopillars comprises a hard plastic characterized by a modulus of at least 10 MPa.

14. The medical device of claim 13, wherein the ability to kill the target bacteria does not stem from chemical modifications to the bactericidal surface.

15. The medical device of claim 13, wherein the bactericidal surface does not include a bactericide and/or silver nanoparticle.

16. The medical device of claim 13, wherein the medical device is selected from the group consisting of: a biomedical implant, surgical trays and instruments, door handles, any implantable medical devices, catheter tubes.

17. A bactericidal substrate characterized by an ability to kill target bacteria upon adhesion to its surface, comprising
   a substrate having a bactericidal surface modified by a pattern comprising a plurality of uniform nanostructures evenly spaced by a plurality of uniform spacings, wherein
      the plurality of uniform nanostructures is characterized by a nanostructure width and a nanostructure periodicity, and
      the plurality of uniform spacings is characterized by a spacing width, wherein the spacing width is a width of a gap between any two adjacent nanostructures as measured at their top edges, and the nanostructure periodicity is a sum of the nanostructure width and the spacing width, and wherein the nanostructure width and the spacing width are each smaller than a width of the target bacteria, wherein the width of the target bacteria is the smallest dimension of the target bacteria, and wherein the nanostructure width, nanostructure periodicity, and the spacing width are adjustable manufacturing parameters, wherein the pattern is configured such that contact by the target bacteria with the top edges of one or more of the plurality of uniform nanopillars immobilizes the target bacteria and causes death of the target bacteria, and wherein the bactericidal surface is characterized by a surface area, and the plurality of uniform nanopillars comprises a hard plastic characterized by a modulus of at least 10 MPa.

18. The bactericidal substrate of claim 17, wherein the plurality of nanostructures comprises nanopillars.

19. The bactericidal substrate of claim 17, wherein the hard plastic is polymethylmethacrylate.

20. The bactericidal substrate of claim 17, wherein the plurality of nanostructures comprises lines and the spacing width is 200 to 300 nm.

21. The bactericidal substrate of claim 17, wherein the plurality of nanostructures comprises lines and the nanostructure width is 20 to 50 nm.

22. The bactericidal substrate of claim 17, wherein the plurality of nanostructures comprises lines and the nanostructure width is 50 to 100 nm.

23. A method of fabricating a bactericidal film, wherein the bactericidal film comprises:

at least one bactericidal surface characterized by an ability to kill target bacteria upon adhesion and comprising:

a surface modified by a pattern comprising a plurality of uniform nanostructures evenly spaced by a plurality of uniform spacings, wherein the plurality of uniform nanostructures is characterized by a nanostructure width and a nanostructure periodicity, and the plurality of uniform spacings is characterized by a spacing width, wherein the spacing width is a width of a gap between any two adjacent nanostructures as measured at their top edges, and the nanostructure periodicity is a sum of the nanostructure width and the spacing width, and wherein the nanostructure width and the spacing width are, each, smaller than a width of the target bacteria, wherein the width of the target bacteria is the smallest dimension of the target bacteria, and wherein the pattern is configured such that contact by the target bacteria with the top edges of one or more of the plurality of uniform nanostructures immobilizes the target bacteria and causes death of the target bacteria;

wherein the method comprises:

providing a flat film of a film thickness and comprising a hard plastic characterized by a modulus of at least 10 MPa and a glass transition temperature;

providing a mold for nanoimprint lithography, wherein the mold comprises a negative of the pattern and is characterized by a mold area;

placing a first surface of the flat film on a support;

pressing the mold against a second surface of the flat film for a first period of time;

releasing the flat film from the mold and the support to produce a free-standing plastic film with at least one bactericidal surface.

24. The method of claim 23, wherein the mold area is at least 176 mm$^2$.

25. The method of claim 23, wherein the mold comprises a material selected from the group consisting of: silicon, metal, hardened polydimethylsiloxane, or another hard plastic.

26. The method of claim 23, wherein pressing of the mold is facilitated by means selected from the group consisting of: heating the flat film to the temperature above the glass transition temperature; heating the mold to the temperature above the glass transition temperature; using the flat film comprising plasticizers; any combination thereof.

27. The method of claim 23, wherein the plurality of nanostructures comprises nanopillars.

28. The method of claim 23, wherein the plurality of nanostructures comprises lines.

29. The method of claim 28, wherein pressing the mold against the second surface for the first period of time is followed by releasing the mold, rotating the mold by 90 degrees, and pressing the mold against the second surface for a second period of time, resulting in the plurality of nanostructures comprising nanopillars with a square cross-section.

30. The method of claim 23, wherein the nanostructure width is up to 500 nm and the nanostructure periodicity is up to 1 µm.

31. The method of claim 23, wherein the spacing width is 10-700 nm.

32. The method of claim 23, wherein the spacing width is less than 500 nm.

33. The method of claim 23, wherein the nanostructure width is 25-700 nm.

34. The method of claim 23, wherein the nanostructure width is less than 500 nm.

35. The method of claim 23, wherein the hard plastic is selected from the group consisting of: polymethylmethacrylate, polycarbonate, polystyrene, polyetherether ketone, polysulfone.

* * * * *